United States Patent [19]

Schwartz et al.

[11] 4,399,160
[45] Aug. 16, 1983

[54] THICKENING COMPOSITION FROM FERMENTED WHEY

[75] Inventors: Robert D. Schwartz, Concord; Elizabeth A. Bodie, El Cerrito, both of Calif.

[73] Assignee: Stauffer Chemical Company, Westport, Conn.

[21] Appl. No.: 290,767

[22] Filed: Aug. 7, 1981

[51] Int. Cl.³ .................. A23C 21/02; A23L 1/28; C12P 19/06; C12N 1/20
[52] U.S. Cl. .................... 426/41; 426/654; 435/103; 435/104; 435/253; 435/910
[58] Field of Search .............. 435/104, 103, 245, 253, 435/910; 426/41, 43, 654

[56] References Cited

U.S. PATENT DOCUMENTS

| | | | |
|---|---|---|---|
| 2,789,911 | 4/1957 | Toulmin, Jr. | 435/103 X |
| 3,044,940 | 7/1962 | Behrens et al. | 435/103 |
| 3,343,962 | 9/1967 | Peer | 435/253 X |
| 3,455,786 | 7/1969 | Miegcher | 435/910 X |
| 3,497,359 | 2/1970 | Peer | 435/41 X |

OTHER PUBLICATIONS

Stauffer, et al., Extracellular Microbial Polysaccharide Production by Fermentation on Whey or Hydrolyzed Whey, J. Food Sci., vol. 43, 1978 (pp. 756–758).
Lundstedt, E., Citrated Whey Starters, J. Da. Sci., vol. 45, 1962 (pp. 1320–1326).
Manual for Dairy Manufacturing Short Courses, Litho. in U.S.A., Kurtz Bros., Clearfield, Pa., 1956 (pp. 56–57).
Lamford et al., Dextran Biosynthesis and Dextronsucrase Production by Continuous Culture of *Leuconostoc mesenteroides*. Biotechnol, and Bio. Eng. vol. XXI, 1979 (pp. 1121–1131).

*Primary Examiner*—David M. Naff
*Attorney, Agent, or Firm*—Michael J. Bradley

[57] ABSTRACT

A synergistic thickening composition for use in foods is prepared by forming a mixture of a dried fermented whey product produced with *Xanthomonas campestris* ATCC 31923 and a dried fermented whey product produced with *Leuconostoc mesenteroides* ATCC 14935.

3 Claims, 3 Drawing Figures

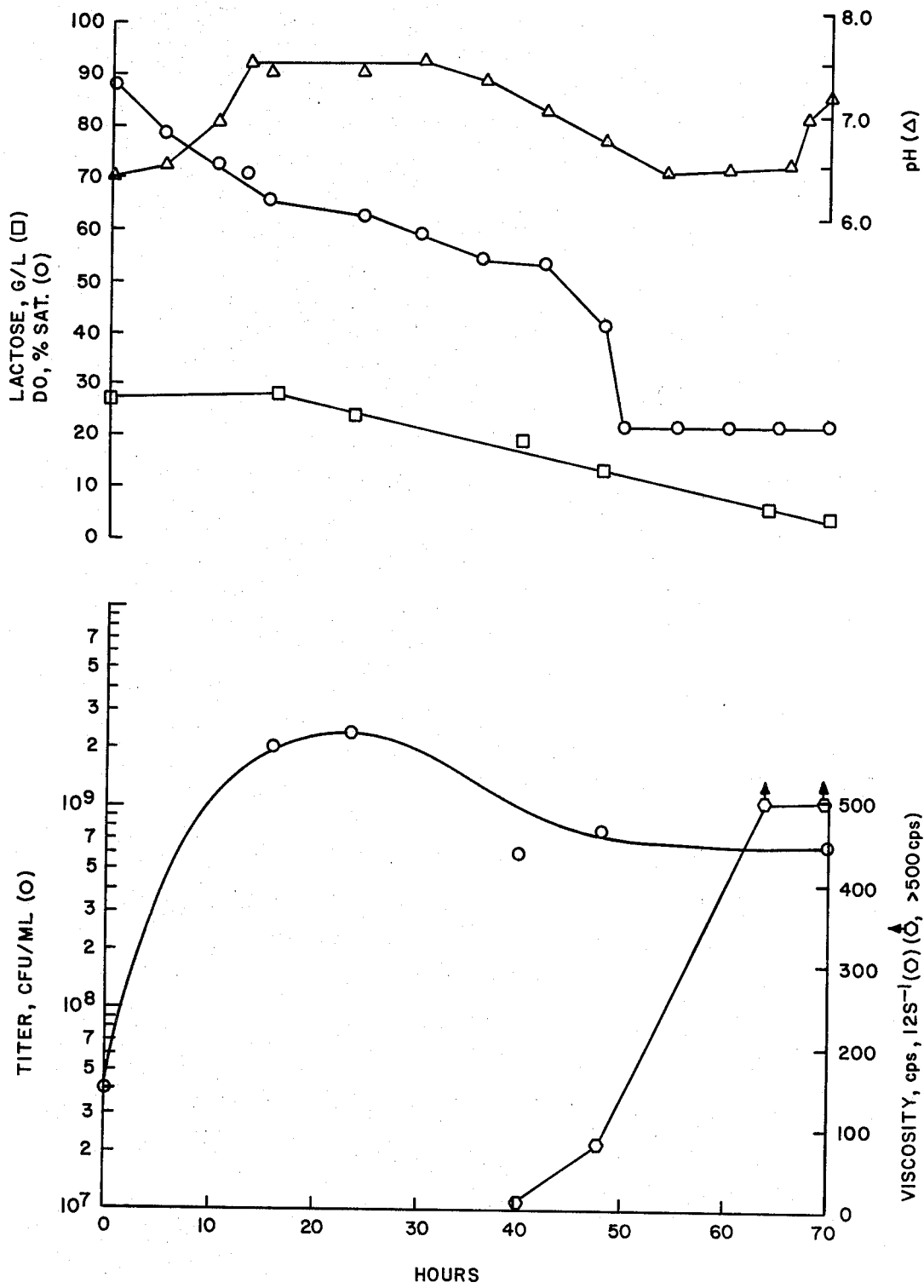
FIGURE I
X. CAMPESTRIS ATCC-31923 FERMENTATION IN WHEY MEDIUM

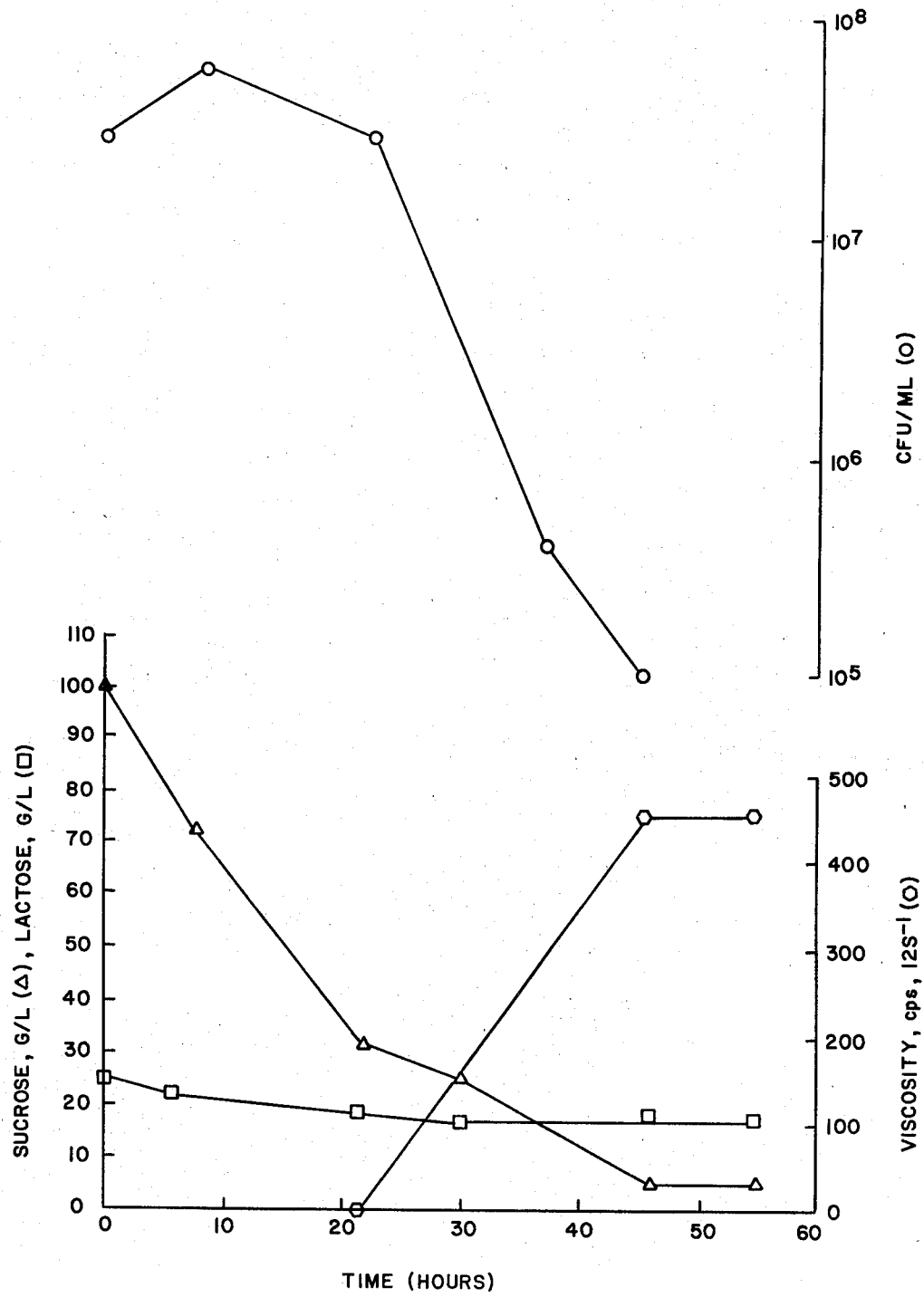
FIGURE II
L. MESENTEROIDES ATCC-14935 FERMENTATION IN WHEY-SUCROSE MEDIUM WITHOUT $K_2HPO_4$

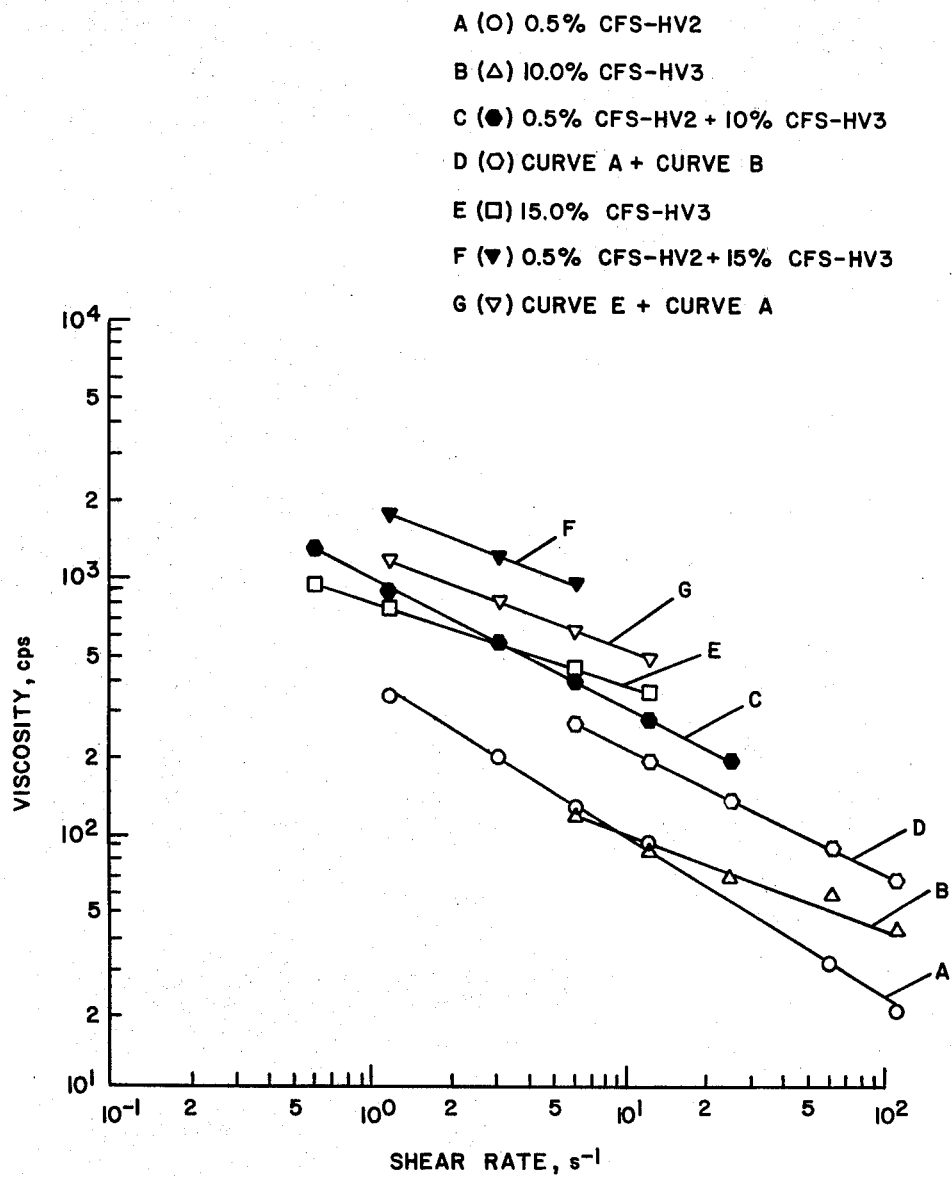

THICKENING COMPOSITION FROM FERMENTED WHEY

BRIEF DESCRIPTION OF THE INVENTION

The process of this invention provides a synergistic thickening composition of matter formed by combining dried functionalized wheys. The wheys utilized are functionalized by different fermentation techniques using different organisms.

BACKGROUND OF THE INVENTION

Controlled fermentation of foods can be used as a means of improving functionality of the foods. Dairy whey, a food, may be an economical source of a fermentable substrate, and is widely used an an accepted milk-derived ingredient in manufactured foods. If whey can be properly functionalized by fermentation with an organism that produces a thickening polymer when grown on the whey substrate, it is possible to obtain whey products that may serve the function of a stabilizer, thickener, emulsifier, or flavor enhancer.

Whey is the fluid medium containing a very low concentration of milk solids and a high concentration of lactose. Disposal of this waste by-product by drying is an energy-intensive, expensive procedure which results in an expensive by-product, while sewering of the whey is prohibitive in cost due to the high biological oxygen demand which is placed on municipal sewer system.

The most desirable method of handling this waste stream is to produce a high quality natural food ingredient from the whey waste product. We have discovered several novel methods of producing a functionalized whey product. We have further discovered that combining two different types of functionalized whey results in a synergistic increase in viscosity. The combined products can be used as a food ingredient or any type of product where milk solids and lactose are acceptable ingredients.

DESCRIPTION OF THE DRAWINGS

FIG. I shows a graph of a typical fermentation of *Xanthomonas campestris* BB-1L (ATCC 31923) in a medium containing 4% Teklac (whey), and 0.05% yeast extract.

FIG. II shows a graph of a fermentation of *Leuconostoc mesenteroides* ATCC 14935 in a medium containing 10% sucrose, 4% Teklac, and 0.05% yeast extract.

FIG. III shows viscosity versus shear rate curves for dried functionalized whey compositions.

DETAILED DESCRIPTION OF THE INVENTION

A functionalized dairy whey wheat product having a viscosity greater than 200 centipoise at a $12s^{-1}$ shear rate for use as a food ingredient that may serve as a stabilizer, thickener, or emulsifier, can be produced by aerobically fermenting a mixture comprising whey, optionally yeast extract and a pH buffer with the novel organism *Xanthomonas campestris* ATCC 31923 to produce a functionalized whey product containing a thickening polymer produced by the novel organism *Xanthomonas campestris* ATCC 31923. This aerobic fermentation can be carried out preferably in a pH range of 6 to 8, preferably with the pH maintained in a range from about 6.5 to about 7.5. The fermentation can be carried out at a temperature from about 20° to 35° C., preferably carried out at a temperature from about 25° to about 30° C. Concentration of whey can range from about 0.5% to about 12.0%, preferably 2% to 4%. The additional yeast extract in the fermentation broth can range from about 0 to about 0.5%, preferably from about 0.01% to about 0.1%. Adequate fermentation broth viscosities (>200 cps and preferably >800 cps at a $12s^{-1}$ shear rate) are usually reached within 48 to 72 hours. All of the above weight percents are in weight per volume. This functionalized whey product is referred to in the drawig and examples as CFS-HV2.

Derivation of *Xanthomonas campestris* ATCC 31923

*X. campestris* ATCC 31923 was isolated for its ability to grow on lactose as sole source of carbon and energy. It was derived from *X. campestris* BB-1 (ATCC 31922) following several serial passages in lactose minimal medium containing 1.5% lactose, 0.5% $K_2HPO_4$, 0.2% $NH_4Cl$, 0.1% NaCl, 0.01% $MgSO_4$, and 0.01% yeast extract. In this medium, at about 28° C., ATCC 31923 has a generation time of about three hours, viable cell titers of about $10^9$/ml or greater are reached, the lactose in the medium is metabolized, and the broth does not become viscous.

When *X. campestris* ATCC 31923 was subsequently grown in whey medium containing 2% Teklac, 0.25% $K_2HPO_4$, 0.01% yeast extract at about 28° C., the generation time was about three hours, viable titers of about $10^9$/ml or greater were reached, the lactose in the medium was metabolized, and the broth became viscous.

Another functionalized whey product can be prepared by fermentation of a whey broth comprising unhydrolyzed whey (acid or sweet), sucrose, and optionally yeast extract and phosphate with the organism *Leuconostoc mesenteroides* ATCC 14935. This fermentation results in polymer formation and functionalization of the whey so that the whey product can be utilized as a food ingredient. This anaerobic fermentation can be carried out preferably in a pH range of 5.5 to 7.5, preferably with the pH maintained in a range from about 6.0 to about 7.0. The fermentation can be carried out at a temperature from about 20° to 35° C., preferably carried out at a temperature from about 25° to about 30° C. Concentration of whey can range from about 0.5% to about 12.0%, preferably from about 1% to about 3%, and the concentration of added sucrose can range from about 5.0% to about 20.0%, preferably 8% to 12%. The additional yeast extract in the fermentation broth can range from about 0 to about 0.5%, preferably from about 0.01% to about 0.05%. Concentration of optional phosphate can range from 0 to about 0.25% $K_2HPO_4$ as desired. Adequate fermentation broth viscosities (>200 cps and preferably >800 cps at a $12s^{-1}$ shear rate) are usually reached within 30 to 50 hours. All of the above weight percents are in weight per volume. This functionalized whey product is referred to in the drawings and examples as CFS-HV3.

Typical composition of Teklac (sweet dairy whey) is as follows:

| CHEMICAL AND PHYSICAL SPECIFICATIONS | |
|---|---|
| Ingredient Listing: Whey | |
| Typical Proximate Analysis | |
| Protein (N × 6.38) % | 12.7 |
| Fat % | 1.1 (1.25% Maximum) |
| Moisture % | 4.5 (5.0% Maximum) |
| Ash % | 8.0 |

-continued

| CHEMICAL AND PHYSICAL SPECIFICATIONS | |
|---|---|
| Ingredient Listing: Whey | |
| Lactose % | 71.3 |
| Calories, Cal/100g | 350.0 |
| Typical Vitamin & Mineral Analysis | |
| Vitamin A I.U./100g | Nil |
| Vitamin C mg/100g | Nil |
| Thiamin mg/100g | 0.40 |
| Riboflavin mg/100g | 1.76 |
| Niacin mg/100g | 1.00 |
| Calcium % | 0.71 |
| Iron % | Nil |
| Vitamin $B_{12}$ ug/100g | 2.12 |
| Phosphorus % | 0.69 |
| Pantothenic Acid mg/100g | 4.09 |
| Microbiological Standards | |
| Standard Plate Count | 10,000/g (Maximum) |
| Coliforms | 9/g (Maximum) |
| E. coli | Negative |
| Salmonella | Negative |

The nutritional values listed above are within 80% of the value declared in compliance with Federal Nutritional Regulations 21 CFR §1.17(4)(ii).

| | Typical Range | Limit |
|---|---|---|
| Solubility Index | 0.1–0.5 ml | 1.25 ml Max. |
| Acidity | 0.10–0.14% | 0.16 Max. |
| Alkalinity of Ash | 175–200 ml | 225 ml Max. |
| Scorched Particles | 7.5 mg | 15.0 mg Max. |
| Particle size (Through 40 Mesh) | 99–100% | 98% Min. |

The literature indicates that synergistic increases in viscosity are observed with the following purified gums: xanthan gum plus guar gum; xanthan gum plus locust bean gum; xanthan gum plus dextrin. Dextran solutions have been reported to have some properties similar to locus bean gum. See, Cottrell, I. W. and K. S. Kang. 1978. Xanthan gum, a Unique Bacterial Polysaccharide for Food Applications. Dev. Industrial, Microbiol. 19:117-131; Kang, K. S. and I. W. cotrell, 1979. Polysaccharides, In *Microbial Technology*, 2nd Ed., Vol. 1, H. J. Pellper and P. Perlmann, eds. Chpa. 13, pp. 417-481. Academic Press, Inc., N.Y.; and Xanthan Gum/Keltrol/Kelzan/A Natural Biopolysaccharide for Scientific Water Control. Kelco Co., San Diego, CA.

The functionalized wheys produced by the above processes can be dried and combined to form synergistic thickening compositions of matter. The concentration of CFS-HV2 can range from about 0.1 to about 4% by weight and preferably from about 0.1 to about 1% by weight. The concentration of CFS-HV3 can range from about 5 to about 25% by weight and preferably from about 10 to 15% by weight.

Examples 1 and 2 show production of CFS-HV2 and CFS-HV3.

EXAMPLE 1

FIG. 1 shows a graph of a typical fermentation of *Xanthomonas campestris* ATCC 31923 in a medium containing 4.0% Teklac and 0.05% yeast extract. The medium was sterilized by autoclaving at 15 pounds per square inch (psi) for 20 minutes. The fermentation was conducted in a fermentor to which air was pumped at the rate of 1 l/l/min, agitation was at the rate of 500 rpm, and the dissolved oxygen concentration maintained at a minimum of 20% saturation. A Bio-flow ® fermentor was used (New Brunswick Scientific Co., N.J.). The initial pH was 7 and was controlled between 6.5 and 7.5. The inoculum was 3% volume/volume from a lactose minimal medium grown culture. The figure shows the general increase in viscosity over time, growth of the organism, and the initial increase in pH, followed by a decrease in pH, typical of this fermentation, and a decrease in lactose concentration.

EXAMPLE 2

FIG. II shows a typical fermentation of a whey-sucrose medium containing 4% Teklac, 10% sucrose, and 0.05% yeast extract. The medium was sterlized by autoclaving at 15 psi for 20 minutes. The sucrose was sterilized and added separately. The pH was adjusted to 7.0 before autoclaving. $NH_4OH$ (6%) was used to prevent the pH from falling below 6.0. The fermentation was anaerobic (no gas sparged), with agitation speed 120 rpm. The temperature was maintained between 25°–27° C. The inoculum was a 20-hour-old culture grown in 10% sucrose, 0.5% $K_2HPO_4$, 0.25% yeast extract, and 0.01% $MgSO_4$. A Bio-flow ® fermentor was used as in Example 1. The figure shows that within 46 hours, a viscosity of 460 cps was obtained. About 95% of the sucrose was utilized and 44% of the lactose was consumed.

The high viscosity broths produced by the above fermentation techniques may be dried and/or sterilized by autoclaving and lyophilization, spray drying, or other techniques.

EXAMPLE 3

FIG. III shows that synergistic increases in viscosity are obtained when functionalized wheys CFS-HV2 and CFS-HV3 are combined. The samples were tested on a 2.5 XLVT Wells-Brookfield microviscometer having a 3° cone at 25° C. The sample size was 2.0 milliliters. CFS-HV2 and CFS-HV3 were dissolved in deionized water at the following concentrations: 0.5% CFS-HV2; 10% CFS-HV3; 0.5% CFS-HV2 plus 10% CFS-HV3; 15% CFS-HV3; 0.5% CFS-HV2 plus 15% CFS-HV3. As shown in FIG. III, the combinations of CFS-HV2 and CFS-HV3 result in at least a 40% increase in viscosity when compared to the individual viscosities obtained when CFS-HV2 and CFS-HV3 are separate and said separate viscosities are added together.

The composition of matter of this invention can be used as a food ingredient where milk solids and/or whey, and/or thickeners, and/or stabilizers are used such as in ice cream, salad dressing, foam stabilizer (meringue), puddings, snack foods, etc. As a result of the synergistic effect observed less CFS-HV2 and CFS-HV3 are required to achieve a desired viscosity than would otherwise be expected.

What is claimed is:

1. A synergistic thickening composition of matter comprising a mixture of:
   (a) from about 0.1 to about 4% by weight of a dried functionalized dairy whey product produced by a process comprising the steps of:
      (1) forming a fermentation broth of whey, and yeast extract, and
      (2) fermenting the broth with the organism *Xanthomonas campestris* ATCC 31923 and
   (b) from about 5 to about 25% by weight of a dried functionalized dairy whey product produced by a process comprising the steps of:

(1) forming a fermentation broth of whey and sucrose; and
(2) fermenting the broth with the organism *Leuconostoc mesenteroides* ATCC 14935.

2. The synergistic thickening composition of claim 1 wherein the mixture comprises from about 0.1 to about 1% by weight of (a) and from about 10 to about 15% by weight of (b).

3. The composition of claim 1 wherein the fermentation broth of step (b)(1) contains yeast extract.

* * * * *